US00PP28399P3

(12) United States Plant Patent
Zaiger et al.

(10) Patent No.: US PP28,399 P3
(45) Date of Patent: Sep. 19, 2017

(54) INTERSPECIFIC TREE NAMED 'AUTUMN BILL'

(50) Latin Name: **Interspecific *Prunus* species**
Varietal Denomination: Autumn Bill

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 114 days.

(21) Appl. No.: 14/757,301

(22) Filed: Dec. 15, 2015

(65) Prior Publication Data

US 2017/0172022 P1 Jun. 15, 2017

(51) Int. Cl.
*A01H 5/08* (2006.01)

(52) U.S. Cl.
USPC ..... Plt./180

(58) Field of Classification Search
USPC ..... Plt./156, 180
See application file for complete search history.

*Primary Examiner* — Susan McCormick Ewoldt
*Assistant Examiner* — Karen Redden

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree having a vigorous, upright growth habit.
2. Tree being a regular and productive bearer of large size, yellow flesh fruit.
3. Fruit with very good flavor and eating quality.
4. Fruit with an attractive, dark red skin color.
5. Fruit with a high degree of soluble solids (Brix) of 18.0°.

1 Drawing Sheet

Botanical designation: Interspecific *Prunus* species.
Variety denomination: 'Autumn Bill'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecific trees, which are known to us, and mentioned herein, 'Fall Fiesta' Interspecific (U.S. Plant Pat. No. 22,428) and our proprietary non-patented interspecific varieties '138LM256', '5HD617', '58LG12', '297LF578', '323LH110' and '20Z177'.

STATEMENT REGARDING FEDERALLY SPONSORED RESEARCH AND DEVELOPMENT

Not applicable.

ORIGIN OF THE VARIETY

The new and distinct variety of interspecific tree was originated by us from crosses between *Prunus salicina, Prunus armeniaca* and *Prunus persica* in our experimental orchard located near Modesto, Calif. as a first generation cross between our proprietary non-patented interspecific seedlings '138LM256' (Plum×Apricot×Peach) and '5HD617' (Plum×Apricot). The seed parent (138LM256) is a first generation cross from our proprietary non-patented interspecific seedlings '58LG12' (Peach×Apricot) and '297LF578' (Plum×Apricot). The pollen parent (5HD617) is a first generation cross from our proprietary non-patented interspecific seedlings '323LH110' (Plum×Apricot) and '20Z177' (Plum×Apricot). A large number of these first generation seedlings were budded onto older established trees of 'Nemaguard' Rootstock (non-patented) to enhance earlier fruit production. Under close and careful observation the present budded seedling exhibited desirable fruit and tree characteristics and was selected in 2008 for additional asexual propagation and commercialization.

ASEXUAL REPRODUCTION OF THE VARIETY

In 2008 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

A new and distinct variety of interspecific tree which consists of Plum, Apricot and Peach has vigorous, upright growth and is a regular and productive bearer of large size fruit with an attractive, dark red skin color. The fruit is further characterized by its firm, yellow flesh, very good flavor and eating quality. In comparison to its proprietary non-patented interspecific seed parent (138LM256) the fruit of the new variety is approximately 74 days later in maturity and has yellow flesh compared to white. In comparison to its proprietary non-patented interspecific pollen parent (5HD617) the fruit of the new variety is approximately 45 days later in maturity and has yellow flesh compared to white. In comparison to the commercial variety 'Fall Fiesta' Interspecific (U.S. Plant Pat. No. 23,428) the fruit of the new variety is approximately 45 days later in maturity.

DESCRIPTION OF THE PHOTOGRAPH

The accompanying color photographic illustration shows typical specimens of the foliage and fruit of the present new interspecific variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 7 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 7 year old specimens grown near Modesto, Calif., with color in accordance with Munsell Book of Color published in 1958.

Tree:

*Size*.—Large, pruned to 3 to 3.5 meters in height and width for economical harvesting of fruit. Varies with different cultural practices.

*Vigor*.—Vigorous, tree growth of 1.5 to 2 meters the first growing season. Varies with cultural practices, soil type, fertility and climatic conditions.

*Form*.—Upright, usually pruned to vase shape.

*Branching habit*.—Upright, crotch angle approximately 30°, increases with heavy crop load.

*Productivity*.—Productive, thinning and spacing of fruit necessary for marketable size fruit. Number of fruit set varies with climatic conditions during blooming period.

*Bearer*.—Regular, has had adequate fruit set 5 consecutive years. No alternate bearing observed.

*Fertility*.—Self-sterile, pollinator required.

*Density*.—Medium dense, usually pruned to vase shape to increase air movement and sunlight to enhance fruit color and health of fruit spurs.

*Hardiness*.—Hardy in all stone fruit growing areas of California. Tree grown in USDA Hardiness Zone 9. Winter chilling requirement approximately 900 hours at or below 45° F.

Trunk:

*Size*.—Medium, average circumference 61.0 cm at 25.4 cm above ground on a 7 year old tree.

*Stocky*.—Medium stocky.

*Texture*.—Medium shaggy, roughness increases with age of tree.

*Color*.—Varies from 7.5YR 6/2 to 10YR 6/2.

Branches:

*Size*.—Medium. Average circumference 9.7 cm at 1.2 meters above ground. Crotch angle approximately 30°, increases with heavy crop load.

*Surface texture*.—New growth relatively smooth. Mature growth medium rough, roughness increases with age.

*Lenticels*.—Average number 30 in a 25.8 square cm area. Average length 3.1 mm. Average width 1.4 mm. Color varies from 5YR 5/12 to 7.5YR 5/10.

*Color*.—New growth varies from 5GY 6/6 to 5GY 5/6. Mature growth varies from 5YR 3/2 to 5YR 2/4, varies with age of growth.

Leaves:

*Size*.—Small to medium. Average length 96.6 mm. Average width 45.5 mm.

*Form*.—Ovate.

*Apex*.—Acuminate.

*Base*.—Cuneate.

*Margin*.—Doubly serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Small. Average length 12.5 mm. Average width 1.5 mm. Surface — glabrous. Longitudinally grooved. Color varies from 5GY 7/6 to 5GY 6/6.

*Glands*.—Type — globose. Size — small. Average length 1.0 mm. Average diameter 0.7 mm. Number varies from 2 to 3, average number 3. Located primarily on the base of the leaf blade and the upper portion of the petiole. Color 5GY 8/6.

*Stipules*.—Average number 2. Average length 7.0 mm. Margin — pectinate. Color varies from 5GY 8/6 to 5GY 7/6.

*Color*.—Upper surface varies from 10Y 3/4 to 10Y 3/2. Lower surface varies from 2.5GY 3/4 to 5GY 4/4. Midvein color varies from 5Y 7/4 to 7.5Y 7/4.

Flower buds:

*Size*.—Medium. Average length 9.1 mm. Average diameter 6.1 mm.

*Hardiness*.—Hardy with respect to California winters.

*Density*.—Medium dense.

*Form*.—Conical, becoming elongated just before opening.

*Pedicel*.—Average length 6.3 mm. Average width 0.8 mm. Surface — glabrous. Color varies from 2.5GY 6/6 to 5GY 7/8.

*Color*.—N 9.5/(white).

*Number of buds per spur*.—Varies from 7 to 10, average number 8.

Flowers:

*Blooming period*.—Date of First Bloom Mar. 4, 2015. Date of Petal Fall Mar. 14, 2015, varies slightly with climatic conditions.

*Size*.—Medium. Average height 11.6 mm. Average diameter 14.9 mm.

*Petals*.—Normally 5, alternately arranged to sepals. Petal apex — rounded. Petal base — truncate. Size — medium. Average length 10.1 mm. Average width 6.7 mm. Form — elliptical. Arrangement — free to slightly overlapping. Margin — sinuate. Color N 9.5/(white). Both upper and lower surfaces glabrous.

*Sepals*.—Normally 5, alternately arranged to petals. Size — medium. Average length 3.3 mm. Average width 2.7 mm. Shape — rounded. Apex — ovate to triangular. Margin — entire. Both upper and lower surfaces glabrous. Color — upper surface varies from 5GY 6/6 to 5GY 6/8. Lower surface varies from 2.5GY 6/8 to 5GY 7/8.

*Stamens*.—Average number per flower 33. Average filament length 8.2 mm. On average the stamens are even with the height of the petals. Filament color N 9.5/(white). Anther color varies from 2.5Y 7/12 to 2.5Y 6/10.

*Pollen*.—Self-sterile, pollinator required. Color varies from 2.5Y 7/12 to 5Y 7/12.

*Pistil*.—Number — normally one. Surface — glabrous. Average length 7.9 mm. Position of stigma an average of 2.2 mm below anthers. Color varies from 10Y 7/6 to 2.5GY 8/6.

*Fragrance*.—Heavy.

*Color*.—N 9.5/(white).

*Pedicel*.—Average length 7.6 mm. Average width 0.8 mm. Surface — glabrous. Color varies from 2.5GY 6/6 to 2.5GY 6/8.

*Number flowers per flower bud*.—Average number 2, varies from 1 to 3.

Fruit:

*Maturity when described*.—Firm ripe and ready for consumption.

*Date of first picking*.—Oct. 15, 2015.

*Date of last picking*.—Oct. 25, 2015, varies slightly with climatic conditions.

*Size*.—Large. Average diameter axially 66.5 mm. Average transversely in suture plane 64.4 mm. Average weight 150.5 grams, varies slightly with fertility of the soil, amount of thinning and climatic conditions.

*Form*.—Globose to slightly elongated.

*Suture*.—Slightly lipped, extends from base to apex.

*Ventral surface*.—Slightly lipped.

*Apex*.—Nearly rounded.

*Base*.—Flat.

*Stem cavity*.—Rounded to slightly elongated in suture plane. Average depth 1.7 mm. Average diameter 3.0 mm.

Stem:

*Size*.—Large. Average length 14.2 mm. Average diameter 2.9 mm.

*Color*.—Varies from 7.5YR 3/4 to 10YR 3/4.

Flesh:

*Ripens*.—Evenly.

*Texture*.—Firm, meaty, crisp.

*Fibers*.—Few, small, tender.

*Firmness*.—Firm, comparable to other commercial interspecific varieties.

*Aroma*.—Moderate.

*Amydgalin*.—Undetected.

*Eating quality*.—Very good.

*Flavor*.—Very good, good balance between acid and sugar.

*Juice*.—Moderate amount, enhances flavor.

*Acidity*.—Not available.

*Brix*.—Average Brix 18.0°, varies slightly with amount of fruit per tree and climatic conditions.

*Color*.—Varies from 2.5Y 7/6 to 5Y 8.5/2.

*Pit cavity*.—Average length 26.6 mm. Average width 21.7 mm. Average depth 6.3 mm. Color varies from 7.5YR 6/10 to 7.5YR 6/8.

Skin:

*Thickness*.—Medium.

*Surface*.—Smooth to slightly waffled.

*Bloom*.—Heavy amount, complete coverage.

*Tendency to crack*.—None.

*Color*.—Ground color varies from 10YR 7/10 to 7.5YR 6/10. Overspread with 5R 2/2 to 7.5R 3/8.

*Tenacity*.—Tenacious to the flesh.

*Astringency*.—Slight to none.

Stone:

*Type*.—Clingstone, medium adherence to flesh.

*Size*.—Medium. Average length 25.6 mm. Average width 20.7 mm. Average thickness 10.6 mm.

*Form*.—Obovoid.

*Base*.—Flat.

*Apex*.—Pointed, average length 2.7 mm.

*Surface*.—Slightly pitted throughout.

*Sides*.—Unequal, one side extending further from suture plane.

*Ridges*.—Very narrow, small ridge near groove on each side of suture, extends from base to apex.

*Tendency to split*.—None.

*Color*.—Varies from 7.5YR 5/8 to 10YR 6/8 when dry.

Kernel:

*Size*.—Small to medium. Average length 16.0 mm. Average width 10.2 mm. Average depth 5.0 mm.

*Form*.—Ovate.

*Viability*.—Viable, complete embryo development.

*Skin color*.—Varies from 7.5YR 4/6 to 10YR 4/6.

Use:

*Dessert*.—Market — local and long distance.

Keeping quality: Good, held firm in cold storage for 3 weeks at 38° to 42° F. without internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices. The present new variety of interspecific tree, its flowers foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

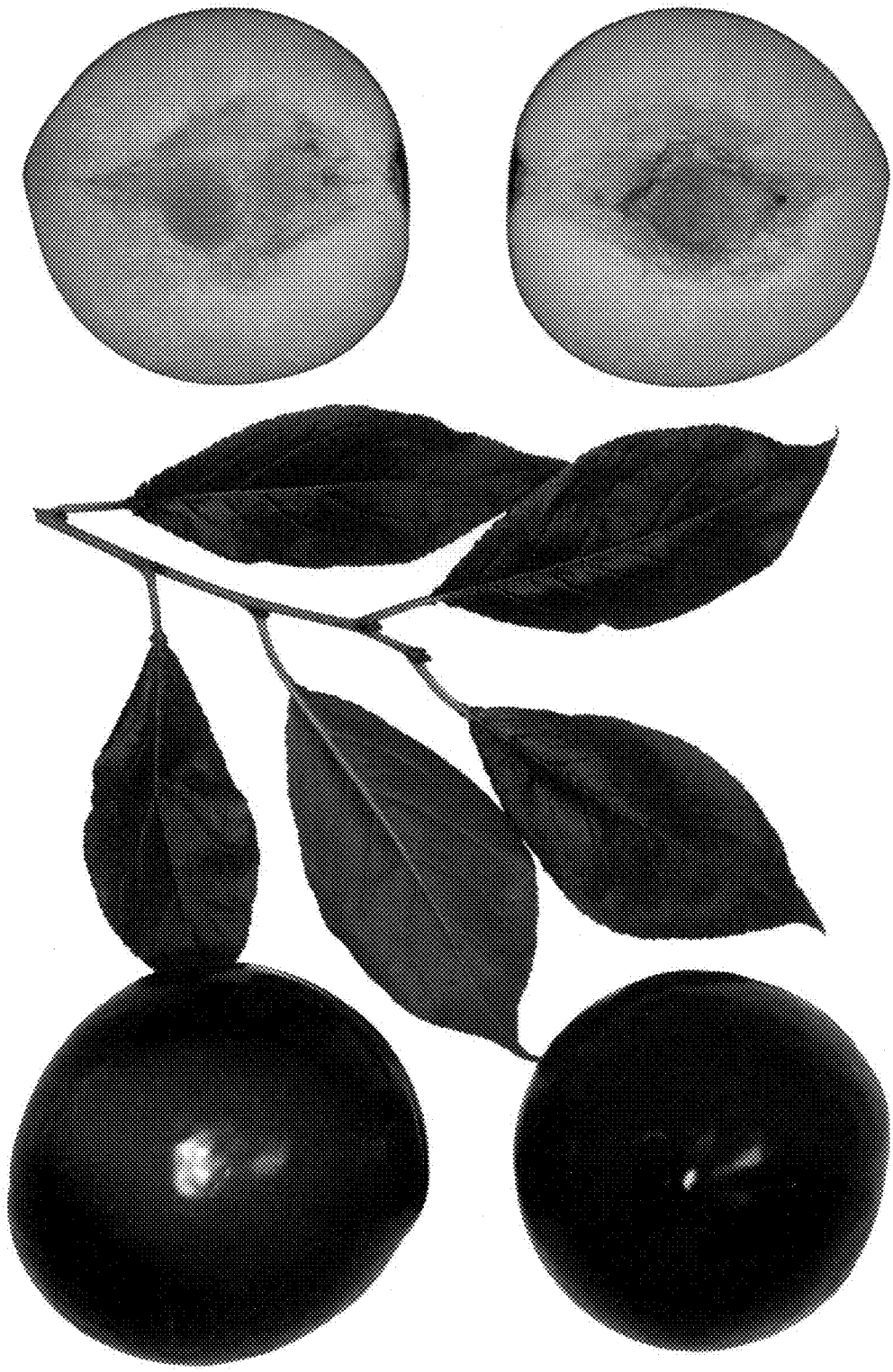

* * * * *